US011278665B2

(12) United States Patent
Zidon et al.

(10) Patent No.: US 11,278,665 B2
(45) Date of Patent: Mar. 22, 2022

(54) METHOD FOR DELIVERING A THERAPEUTIC SUBSTANCE

(71) Applicant: EITAN MEDICAL LTD., Netanya (IL)

(72) Inventors: Shahar Zidon, Kibbutz Shefayim (IL); Boaz Eitan, Hofit (IL); Ori Ben-David, Tel Aviv (IL); Andrei Yosef, Even Yehuda (IL)

(73) Assignee: EITAN MEDICAL LTD., Netanya (IL)

(*) Notice: Subject to any disclaimer, the term of this patent is extended or adjusted under 35 U.S.C. 154(b) by 299 days.

(21) Appl. No.: 16/462,458

(22) PCT Filed: Nov. 22, 2017

(86) PCT No.: PCT/IL2017/051276
§ 371 (c)(1),
(2) Date: May 20, 2019

(87) PCT Pub. No.: WO2018/096534
PCT Pub. Date: May 31, 2018

(65) Prior Publication Data
US 2019/0365985 A1 Dec. 5, 2019

Related U.S. Application Data

(60) Provisional application No. 62/425,105, filed on Nov. 22, 2016.

(51) Int. Cl.
A61M 5/142 (2006.01)
A61M 5/168 (2006.01)

(52) U.S. Cl.
CPC .... A61M 5/14216 (2013.01); A61M 5/14248 (2013.01); A61M 5/16809 (2013.01);
(Continued)

(58) Field of Classification Search
CPC .......... A61M 5/14216; A61M 5/14212; A61M 5/14248; A61M 5/16809; A61M 5/16827;
(Continued)

(56) References Cited

U.S. PATENT DOCUMENTS 3,469,578 A  9/1969 Bierman
3,993,061 A * 11/1976 O'Leary ........... A61M 5/14216
                                                604/152

(Continued)

FOREIGN PATENT DOCUMENTS

EP     0223451     5/1987
EP     0268480     5/1988
(Continued)

OTHER PUBLICATIONS

An International Search Report and a Written Opinion both dated Jan. 19, 2018, which issued during the prosecution of Applicant's PCT/IL2017/051276.

(Continued)

Primary Examiner — James D Ponton
(74) Attorney, Agent, or Firm — Sughrue Mion, PLLC

(57) ABSTRACT

Apparatus is provided including a therapeutic substance reservoir (24) configured to hold a therapeutic substance (22), and an electromechanical pumping assembly (26). The pumping assembly is shaped to define a pump chamber (28) having (a) a therapeutic substance inlet (30), and (b) a therapeutic substance outlet (32). The pumping assembly includes a plunger (34) disposed such that therapeutic substance in the pump chamber is in direct contact with the plunger, and control circuitry (36) configured to drive the plunger to (a) draw the therapeutic substance into the pump chamber during a first pumping phase, and (b) deliver the
(Continued)

therapeutic substance from the pump chamber in a plurality of discrete motions of the plunger during a second pumping phase.

4 Claims, 12 Drawing Sheets

(52) U.S. Cl.
CPC ............... *A61M 5/16827* (2013.01); *A61M 2005/14208* (2013.01)

(58) Field of Classification Search
CPC ............ A61M 5/14208; A61M 5/1407; A61M 5/1408; A61M 5/2448; A61M 5/2066; A61M 5/284; A61M 5/31596; F04B 13/00; F04B 13/02; F04B 49/08; F04B 49/12; F04B 49/20; F04B 15/00; F04B 15/02
See application file for complete search history.

(56) References Cited

U.S. PATENT DOCUMENTS

| | | | |
|---|---|---|---|
| 4,511,355 A | 4/1985 | Franetzki et al. | |
| 4,585,435 A | 4/1986 | Vaillancourt | |
| 4,909,790 A | 3/1990 | Tsujikawa et al. | |
| 4,968,301 A | 11/1990 | Di Palma et al. | |
| 5,085,656 A | 2/1992 | Polaschegg | |
| 5,129,884 A | 7/1992 | Dysarz | |
| 5,178,610 A | 1/1993 | Tsujikawa et al. | |
| 5,207,645 A | 5/1993 | Ross et al. | |
| 5,242,406 A | 9/1993 | Gross et al. | |
| 5,242,411 A | 9/1993 | Yamamoto et al. | |
| 5,324,258 A | 6/1994 | Rohrbough | |
| 5,439,355 A * | 8/1995 | Jimison ............ A61M 5/16854 417/63 |
| 5,708,367 A | 1/1998 | Tousson | |
| 5,785,688 A | 7/1998 | Joshi et al. | |
| 5,897,530 A | 4/1999 | Jackson | |
| 5,919,167 A | 7/1999 | Mulhauser et al. | |
| 5,993,423 A | 11/1999 | Choi | |
| 6,086,561 A | 7/2000 | Kriesel | |
| 6,146,109 A | 11/2000 | Davis et al. | |
| 6,171,276 B1 | 1/2001 | Lippe et al. | |
| 6,186,982 B1 | 2/2001 | Gross et al. | |
| 6,227,807 B1 | 5/2001 | Chase | |
| 6,248,093 B1 | 6/2001 | Moberg | |
| 6,293,159 B1 | 9/2001 | Kriesel et al. | |
| 6,362,591 B1 | 3/2002 | Moberg | |
| 6,468,261 B1 | 10/2002 | Small et al. | |
| 6,485,461 B1 | 11/2002 | Mason et al. | |
| 6,485,465 B2 | 11/2002 | Moberg et al. | |
| 6,530,217 B1 | 3/2003 | Yokota et al. | |
| 6,530,900 B1 | 3/2003 | Daily et al. | |
| 6,542,350 B1 | 4/2003 | Rogers | |
| 6,555,986 B2 | 4/2003 | Moberg | |
| 6,656,158 B2 | 12/2003 | Mahoney et al. | |
| 6,656,159 B2 | 12/2003 | Flaherty | |
| 6,659,980 B2 | 12/2003 | Moberg et al. | |
| 6,669,669 B2 | 12/2003 | Flaherty et al. | |
| 6,673,035 B1 | 1/2004 | Rice et al. | |
| 6,680,597 B1 | 1/2004 | Catellani et al. | |
| 6,699,218 B2 | 3/2004 | Flaherty et al. | |
| 6,740,059 B2 | 5/2004 | Flaherty | |
| 6,749,403 B2 | 6/2004 | Bryant et al. | |
| 6,853,160 B1 | 2/2005 | Gandel et al. | |
| 6,979,316 B1 | 12/2005 | Rubin et al. | |
| 7,029,455 B2 | 4/2006 | Flaherty | |
| 7,052,251 B2 | 5/2006 | Nason et al. | |
| 7,115,108 B2 | 10/2006 | Wilkinson et al. | |
| 7,137,964 B2 | 11/2006 | Flaherty | |
| 7,144,384 B2 | 12/2006 | Gorman et al. | |
| 7,278,981 B2 | 10/2007 | Ellingboe et al. | |
| 7,303,549 B2 | 12/2007 | Flaherty et al. | |
| 7,390,314 B2 | 6/2008 | Stutz, Jr. et al. | |
| 7,442,186 B2 | 10/2008 | Blomquist | |
| 7,455,664 B2 | 11/2008 | Fleury et al. | |
| 7,466,092 B2 | 12/2008 | Prudham | |
| 7,503,278 B2 | 3/2009 | Sigg et al. | |
| 7,524,304 B2 | 4/2009 | Genosar | |
| 7,530,964 B2 | 5/2009 | Lavi et al. | |
| 7,556,623 B2 | 7/2009 | Lyman et al. | |
| 7,591,448 B2 | 9/2009 | Martin et al. | |
| 7,621,893 B2 | 11/2009 | Moberg et al. | |
| 7,682,338 B2 | 3/2010 | Griffin | |
| 7,736,338 B2 | 6/2010 | Kavazov et al. | |
| 7,766,873 B2 | 8/2010 | Moberg et al. | |
| 7,771,412 B2 | 8/2010 | Anderson et al. | |
| 7,887,505 B2 | 2/2011 | Flaherty | |
| 7,892,206 B2 | 2/2011 | Moberg et al. | |
| 7,918,825 B2 | 4/2011 | O'connor et al. | |
| 7,918,843 B2 | 4/2011 | Genosar et al. | |
| 7,931,643 B2 | 4/2011 | Olsen et al. | |
| 7,937,831 B2 | 5/2011 | Sigg et al. | |
| 7,976,505 B2 | 7/2011 | Hines et al. | |
| 7,981,085 B2 | 7/2011 | Ethelfeld | |
| 8,062,253 B2 | 11/2011 | Nielsen et al. | |
| 8,062,257 B2 | 11/2011 | Moberg et al. | |
| 8,065,096 B2 | 11/2011 | Moberg et al. | |
| 8,072,209 B2 | 12/2011 | Jerance et al. | |
| 8,081,069 B2 | 12/2011 | Haueter et al. | |
| 8,088,096 B2 | 1/2012 | Lauchard et al. | |
| 8,105,280 B2 | 1/2012 | Iddan et al. | |
| 8,128,597 B2 | 3/2012 | Cross et al. | |
| 8,129,474 B2 | 3/2012 | Ohbi | |
| 8,140,275 B2 | 3/2012 | Campbell et al. | |
| 8,152,779 B2 | 4/2012 | Cabiri et al. | |
| 8,172,804 B2 | 5/2012 | Bikovsky | |
| 8,182,447 B2 | 5/2012 | Moberg et al. | |
| 8,202,250 B2 | 6/2012 | Stutz, Jr. | |
| 8,222,777 B2 | 7/2012 | Loussert et al. | |
| 8,226,610 B2 | 7/2012 | Edwards et al. | |
| 8,231,572 B2 | 7/2012 | Carter et al. | |
| 8,246,573 B2 * | 8/2012 | Ali ................... A61M 5/14212 604/65 |
| 8,267,893 B2 | 9/2012 | Moberg et al. | |
| 8,281,656 B2 | 10/2012 | Schnidrig | |
| 8,285,328 B2 | 10/2012 | Caffey et al. | |
| 8,294,561 B2 | 10/2012 | Strahm et al. | |
| 8,298,171 B2 | 10/2012 | Ishikawa et al. | |
| 8,303,535 B2 | 11/2012 | Both et al. | |
| 8,347,807 B2 | 1/2013 | Sigg et al. | |
| 8,372,045 B2 | 2/2013 | Needle et al. | |
| 8,427,095 B2 | 4/2013 | Bilat et al. | |
| 8,435,214 B2 | 5/2013 | Gray et al. | |
| 8,444,592 B2 | 5/2013 | Williams et al. | |
| 8,449,502 B2 | 5/2013 | Pratt et al. | |
| 8,465,468 B1 | 6/2013 | Pettis et al. | |
| 8,467,980 B2 | 6/2013 | Campbell et al. | |
| 8,480,622 B2 | 7/2013 | Kawamura | |
| 8,483,980 B2 | 7/2013 | Moberg et al. | |
| 8,486,018 B2 | 7/2013 | Kamen et al. | |
| 8,502,426 B2 | 8/2013 | Loussert et al. | |
| 8,523,803 B1 | 9/2013 | Favreau | |
| 8,603,026 B2 | 12/2013 | Favreau | |
| 8,603,027 B2 | 12/2013 | Favreau | |
| 8,617,110 B2 | 12/2013 | Moberg et al. | |
| 8,636,696 B2 | 1/2014 | Ross et al. | |
| 8,647,074 B2 | 2/2014 | Moberg et al. | |
| 8,647,296 B2 | 2/2014 | Moberg et al. | |
| 8,668,672 B2 | 3/2014 | Moberg et al. | |
| 8,681,010 B2 | 3/2014 | Moberg et al. | |
| 8,702,656 B2 | 4/2014 | Kamen et al. | |
| 8,708,959 B2 | 4/2014 | Haase | |
| 8,708,994 B2 | 4/2014 | Pettis et al. | |
| 8,729,912 B2 | 5/2014 | Cefai et al. | |
| 8,752,570 B2 | 6/2014 | Donahue | |
| 8,784,403 B2 | 7/2014 | Cefai et al. | |
| 8,795,234 B2 | 8/2014 | Kadamus et al. | |
| 8,808,269 B2 | 8/2014 | Bazargan et al. | |
| 8,821,432 B2 | 9/2014 | Unverdorben | |
| 8,834,420 B2 | 9/2014 | Estes et al. | |

(56) References Cited

U.S. PATENT DOCUMENTS

| | | |
|---|---|---|
| 8,834,454 B2 | 9/2014 | Genosar et al. |
| 8,858,511 B2 | 10/2014 | Gonnelli et al. |
| 8,864,739 B2 | 10/2014 | Moberg et al. |
| 8,890,380 B2 | 11/2014 | Andrieux et al. |
| 8,900,188 B2 | 12/2014 | Blumberg, Jr. et al. |
| 8,905,966 B2 | 12/2014 | Yoh et al. |
| 8,905,970 B2 | 12/2014 | Bates et al. |
| 8,920,367 B2 | 12/2014 | Edwards et al. |
| 8,920,376 B2 | 12/2014 | Caffey et al. |
| 8,920,386 B2 | 12/2014 | Cefai et al. |
| 8,957,674 B2 | 2/2015 | Genoud et al. |
| 8,970,384 B2 | 3/2015 | Yodfat et al. |
| 8,998,850 B2 | 4/2015 | Kamen et al. |
| 8,998,851 B2 | 4/2015 | Constantineau et al. |
| 9,011,371 B2 | 4/2015 | Moberg et al. |
| 9,033,925 B2 | 5/2015 | Moberg et al. |
| 9,050,406 B2 | 6/2015 | Kow et al. |
| 9,061,097 B2 | 6/2015 | Holt et al. |
| 9,089,637 B2 | 7/2015 | Chong et al. |
| 9,107,998 B2 | 8/2015 | Pratt et al. |
| 9,107,999 B2 | 8/2015 | Moberg et al. |
| 9,180,244 B2 | 11/2015 | Anderson et al. |
| 9,227,010 B2 | 1/2016 | Neta et al. |
| 9,227,019 B2 | 1/2016 | Swift et al. |
| 9,238,112 B2 | 1/2016 | Schoonmaker et al. |
| 9,242,052 B2 | 1/2016 | Pettis et al. |
| 9,250,111 B2 | 2/2016 | Whalley et al. |
| 9,283,322 B2 | 3/2016 | Shih et al. |
| 9,327,073 B2 | 5/2016 | Moberg et al. |
| 9,333,297 B2 | 5/2016 | Li et al. |
| 9,344,024 B2 | 5/2016 | Favreau |
| 9,364,608 B2 | 6/2016 | Moberg et al. |
| 9,379,652 B2 | 6/2016 | Favreau |
| 9,379,653 B2 | 6/2016 | Favreau |
| 9,381,299 B2 | 7/2016 | Kuo et al. |
| 9,402,950 B2 | 8/2016 | Dilanni et al. |
| 9,402,951 B2 | 8/2016 | Geipel et al. |
| 9,415,158 B2 | 8/2016 | Miller et al. |
| 9,433,732 B2 | 9/2016 | Moberg et al. |
| 9,433,733 B2 | 9/2016 | Moberg et al. |
| 9,446,185 B2 | 9/2016 | Yodfat et al. |
| 9,452,261 B2 | 9/2016 | Alon |
| 9,463,280 B2 | 10/2016 | Cabiri et al. |
| 9,480,624 B2 | 11/2016 | Holt et al. |
| 9,492,613 B2 | 11/2016 | Kamen et al. |
| 9,492,614 B2 | 11/2016 | Kamen et al. |
| 9,498,587 B2 | 11/2016 | Gray |
| 9,504,785 B2 | 11/2016 | Forsell et al. |
| 9,545,474 B2 | 1/2017 | Hanson et al. |
| 9,592,336 B2 | 3/2017 | Nielsen et al. |
| 9,616,171 B2 | 4/2017 | Qin et al. |
| 9,623,174 B2 | 4/2017 | Pang et al. |
| 9,636,451 B2 | 5/2017 | Gonnelli et al. |
| 9,649,433 B2 | 5/2017 | Lanier, Jr. et al. |
| 9,662,271 B2 | 5/2017 | Holt et al. |
| 9,687,186 B2 | 6/2017 | Goldstein et al. |
| 9,717,857 B2 | 8/2017 | Lanier |
| 9,724,462 B2 | 8/2017 | Rotem |
| 9,744,297 B2 | 8/2017 | Cabiri et al. |
| 9,744,304 B2 | 8/2017 | Swift et al. |
| 9,750,871 B2 | 9/2017 | Metzmaker et al. |
| 9,750,875 B2 | 9/2017 | Smith et al. |
| 9,750,953 B2 | 9/2017 | Kalafut |
| 9,782,545 B2 | 10/2017 | Gross et al. |
| 9,795,735 B2 | 10/2017 | Levesque et al. |
| 9,812,918 B2 | 11/2017 | Andrieux |
| 9,813,985 B2 | 11/2017 | Shapley et al. |
| 9,821,117 B2 | 11/2017 | Anderson et al. |
| 9,849,238 B2 | 12/2017 | Li et al. |
| 9,861,769 B2 | 1/2018 | Kamen et al. |
| 9,861,801 B2 | 1/2018 | Baker et al. |
| 9,867,929 B2 | 1/2018 | Searle et al. |
| 9,878,091 B2 | 1/2018 | Cabiri |
| 9,881,367 B1 | 1/2018 | Milne et al. |
| 9,889,256 B2 | 2/2018 | Cabiri et al. |
| 9,901,672 B2 | 2/2018 | Despa et al. |
| 9,940,440 B2 | 4/2018 | Ali et al. |
| 9,943,643 B2 | 4/2018 | Constantineau et al. |
| 9,950,110 B2 | 4/2018 | Mandro et al. |
| 9,956,345 B2 | 5/2018 | Anderson et al. |
| 9,987,428 B2 | 6/2018 | Tan-malecki et al. |
| 9,999,724 B2 | 6/2018 | Cindrich et al. |
| 10,010,674 B2 | 7/2018 | Rosinko et al. |
| 10,029,046 B2 | 7/2018 | Haueter et al. |
| 10,034,976 B2 | 7/2018 | Vazquez et al. |
| 10,034,977 B2 | 7/2018 | Haueter et al. |
| 10,034,983 B2 | 7/2018 | Haueter et al. |
| 10,071,209 B2 | 9/2018 | Solomon et al. |
| 10,088,660 B2 | 10/2018 | Fradkin et al. |
| 10,092,703 B2 | 10/2018 | Mounce et al. |
| 10,092,706 B2 | 10/2018 | Denzer et al. |
| 10,112,005 B2 | 10/2018 | Rotem et al. |
| 10,124,112 B2 | 11/2018 | Diianni et al. |
| 10,130,758 B2 | 11/2018 | Diianni et al. |
| 10,141,882 B2 | 11/2018 | Favreau |
| 10,183,156 B2 | 1/2019 | Ross et al. |
| 10,195,342 B2 | 2/2019 | Cole et al. |
| 10,220,147 B2 | 3/2019 | Constantineau et al. |
| 10,228,663 B2 | 3/2019 | Favreau |
| 10,232,108 B2 | 3/2019 | Qi et al. |
| 10,245,377 B2 | 4/2019 | Mclaughlin |
| 10,272,197 B2 | 4/2019 | Shapley et al. |
| 10,272,200 B2 | 4/2019 | Shapley et al. |
| 10,279,129 B2 | 5/2019 | Shay |
| 10,314,976 B2 | 6/2019 | Tan-malecki et al. |
| 10,335,542 B2 | 7/2019 | Rotem |
| 10,342,926 B2 | 7/2019 | Nazzaro et al. |
| 10,363,342 B2 | 7/2019 | Dillon et al. |
| 10,363,372 B2 | 7/2019 | Nazzaro |
| 10,363,374 B2 | 7/2019 | Nazzaro et al. |
| 10,391,237 B2 | 8/2019 | Cefai et al. |
| 10,391,239 B2 | 8/2019 | Lorenzen et al. |
| 10,398,854 B2 | 9/2019 | Fenster et al. |
| 10,413,665 B2 | 9/2019 | Rioux et al. |
| 10,420,883 B2 | 9/2019 | Diianni et al. |
| 10,438,696 B2 | 10/2019 | Shapley et al. |
| 10,438,698 B2 | 10/2019 | Pillalamarri et al. |
| 10,441,717 B2 | 10/2019 | Schmid et al. |
| 10,441,723 B2 | 10/2019 | Nazzaro |
| 10,448,885 B2 | 10/2019 | Schmid |
| 10,449,290 B2 | 10/2019 | Shapley et al. |
| 10,478,550 B2 | 11/2019 | Hadvary et al. |
| 10,492,990 B2 | 12/2019 | Mounce et al. |
| 10,561,797 B2 | 2/2020 | Nazzaro et al. |
| 10,569,014 B2 | 2/2020 | Hanson et al. |
| 10,625,018 B2 | 4/2020 | Destefano et al. |
| 10,646,652 B2 | 5/2020 | Mccullough et al. |
| 10,668,227 B2 | 6/2020 | Caspers |
| 10,729,852 B2 | 8/2020 | Baker et al. |
| 10,737,024 B2 | 8/2020 | Schmid |
| 10,765,801 B2 | 9/2020 | Mccullough |
| 10,814,062 B2 | 10/2020 | Gyory |
| 2003/0014014 A1 | 1/2003 | Nitzan |
| 2003/0065287 A1 | 4/2003 | Spohn et al. |
| 2003/0109827 A1 | 6/2003 | Lavi et al. |
| 2004/0010207 A1 | 1/2004 | Flaherty et al. |
| 2004/0013538 A1* | 1/2004 | Fuchs .................. F02M 59/02 417/295 |
| 2004/0015042 A1 | 1/2004 | Vincent et al. |
| 2004/0064101 A1 | 4/2004 | Kowan et al. |
| 2004/0162521 A1 | 8/2004 | Bengtsson |
| 2005/0147508 A1* | 7/2005 | Luongo .................. F04B 51/00 417/415 |
| 2005/0203461 A1 | 9/2005 | Flaherty et al. |
| 2008/0051738 A1 | 2/2008 | Griffin |
| 2009/0036867 A1 | 2/2009 | Glejboel et al. |
| 2009/0254041 A1 | 10/2009 | Krag et al. |
| 2010/0137830 A1 | 6/2010 | Glejboel et al. |
| 2010/0227818 A1 | 9/2010 | Bock et al. |
| 2010/0292632 A1 | 11/2010 | Mulvihill et al. |
| 2011/0230826 A1 | 9/2011 | Yoh et al. |
| 2012/0022499 A1 | 1/2012 | Anderson et al. |
| 2013/0090633 A1 | 4/2013 | Loeb |

(56) References Cited

U.S. PATENT DOCUMENTS

| | | | |
|---|---|---|---|
| 2014/0088554 A1* | 3/2014 | Li | A61M 5/14248 604/506 |
| 2014/0142508 A1 | 5/2014 | Diianni et al. | |
| 2014/0163477 A1 | 6/2014 | Quinn et al. | |
| 2014/0214010 A1 | 7/2014 | Kuo et al. | |
| 2015/0029816 A1* | 1/2015 | Beyer | B01F 15/00487 366/167.1 |
| 2015/0141920 A1 | 5/2015 | O'connor et al. | |
| 2016/0000999 A1 | 1/2016 | Focht et al. | |
| 2016/0177937 A1* | 6/2016 | Liu | F04B 49/022 417/44.2 |
| 2016/0184516 A1 | 6/2016 | Shih et al. | |
| 2016/0369789 A1 | 12/2016 | Alderete, Jr. et al. | |
| 2017/0189609 A1 | 7/2017 | Wei | |
| 2017/0281877 A1 | 10/2017 | Marlin et al. | |
| 2018/0085517 A1 | 3/2018 | Laurence et al. | |
| 2019/0151544 A1 | 5/2019 | Stonecipher | |
| 2019/0365990 A1 | 12/2019 | Phillips et al. | |
| 2020/0113515 A1 | 4/2020 | O'connor et al. | |

FOREIGN PATENT DOCUMENTS

| | | |
|---|---|---|
| EP | 0293958 A1 | 12/1988 |
| EP | 0380862 | 8/1990 |
| EP | 0464761 | 1/1992 |
| EP | 0937477 A2 | 8/1999 |
| EP | 0555007 | 12/1999 |
| EP | 2060284 | 5/2009 |
| EP | 1677729 | 7/2009 |
| EP | 2134388 | 12/2012 |
| EP | 2902052 | 8/2015 |
| EP | 3354303 | 8/2018 |
| WO | 2000/069507 | 11/2000 |
| WO | 2007/077255 | 7/2007 |
| WO | 2008/107378 | 9/2008 |
| WO | 2010/096449 | 8/2010 |
| WO | 2012126744 A1 | 9/2012 |
| WO | 2013/184646 | 12/2013 |
| WO | 2015/038556 | 3/2015 |
| WO | 2015/048093 | 4/2015 |
| WO | 2016/164349 | 10/2016 |
| WO | 2017/192287 | 11/2017 |
| WO | 2019/159121 | 8/2019 |

OTHER PUBLICATIONS

Extended European Search Report dated Sep. 11, 2020 in European Application No. 20187553.1.

An International Search Report and a Written Opinion both dated Jun. 9, 2020, which issued during the prosecution of PCT/IL2020/050246.

European Search Report dated Dec. 12, 2019, which issued during the prosecution of Applicant's European App No. 19201363.9.

U.S. Appl. No. 61/940,601, filed Feb. 17, 2014.

An Office Action dated Dec. 3, 2021, which issued during the prosecution of U.S. Appl. No. 16/591,848.

* cited by examiner

METHOD FOR DELIVERING A THERAPEUTIC SUBSTANCE

CROSS-REFERENCE TO RELATED APPLICATIONS

The present application is the US national stage application of PCT/IL2017/051276, filed Nov. 22, 2017, which published as PCT Publication WO 2018/096534 to Zidon, and which claims the priority of U.S. 62/425,105 to Tzidon, filed Nov. 22, 2016 entitled, "Methods circuits assemblies devices and functionally associated machine associated code for wearable drug delivery systems," which is incorporated herein by reference.

The above-referenced applications are incorporated herein by reference.

FIELD OF THE INVENTION

The present invention relates generally to delivery of a therapeutic substance to a subject, and more specifically to wearable drug delivery devices.

BACKGROUND

Pumps are often used in the medical industry for delivering therapeutic substances, e.g., drugs, to subjects. Therapeutic substances such as saline solution, insulin, antibiotics, and chemotherapy drugs may all be delivered to a subject with medical pumps. While hospitalization is required for delivery of some therapeutic substances, other therapeutic substances, such as for example insulin, do not require that the subject be in the hospital. Medical pumps enable patients to go about their daily lives while receiving a therapeutic substance.

SUMMARY OF THE INVENTION

Apparatus, such as for example a wearable medical patch pump, is provided for delivering a therapeutic substance to a subject in a precise, controlled, and consistent manner. In accordance with some applications of the present invention, the apparatus includes a therapeutic substance reservoir for holding the therapeutic substance, and an electromechanical pumping assembly coupled to the reservoir for delivery of the therapeutic substance to the subject. The electromechanical pumping assembly is shaped to define a pump chamber having a therapeutic substance inlet and a therapeutic substance outlet. The therapeutic substance is received from the reservoir into the pump chamber through the therapeutic substance inlet during a first pumping phase, and is delivered from the pump chamber to the subject through the therapeutic substance outlet during a second pumping phase. The electromechanical pumping assembly uses a plunger that is disposed such that therapeutic substance in the pump chamber is in direct contact with the plunger. Control circuitry drives the plunger to (a) draw the therapeutic substance into the pump chamber during the first pumping phase and (b) deliver the therapeutic substance from the pump chamber in a plurality of discrete motions of the plunger during the second pumping phase, thereby delivering the therapeutic substance to the subject in a plurality of controlled and discrete dosages throughout the second pumping phase. A cycle of alternating the first and second pumping phases may be repeated as many times as desired.

There is therefore provided, in accordance with some applications of the present invention, apparatus for delivering a therapeutic substance to a subject, the apparatus including:
  a therapeutic substance reservoir configured to hold a therapeutic substance; and
  an electromechanical pumping assembly coupled to the reservoir, the pumping assembly shaped to define a pump chamber having:
    (a) a therapeutic substance inlet through which the therapeutic substance is received from the reservoir into the pump chamber during a first pumping phase of the pumping assembly, and
    (b) a therapeutic substance outlet through which the therapeutic substance is delivered from the pump chamber to the subject during a second pumping phase of the pumping assembly,
  the pumping assembly including:
    a plunger disposed such that therapeutic substance in the pump chamber is in direct contact with the plunger; and
    control circuitry configured to drive the plunger to (a) draw the therapeutic substance into the pump chamber during the first pumping phase, and (b) deliver the therapeutic substance from the pump chamber in a plurality of discrete motions of the plunger during the second pumping phase.

For some applications, the control circuitry is configured to drive the plunger to draw the therapeutic substance into the pump chamber during the first pumping phase in a single motion of the plunger.

For some applications, the control circuitry is configured to drive the plunger to draw the therapeutic substance into the pump chamber during the first pumping phase in one or more discrete expansion motions of the plunger, a duration of each expansion motion being longer than a duration of any one of the plurality of discrete motions of the plunger during the second pumping phase.

For some applications, the control circuitry is configured to drive the plunger such that respective durations of the plurality of discrete motions of the plunger during the second pumping phase are equal.

For some applications, the control circuitry is configured to drive the plunger such that a duration of the first pumping phase and a duration of the second pumping phase are unequal.

For some applications, a ratio of the duration of the second pumping phase to the duration of the first pumping phase is at least 10:1.

For some applications, a ratio of a duration of the second pumping phase to a duration of the first pumping phase is between 5:1 and 50:1.

For some applications, the apparatus further includes (a) an inlet valve coupled to the therapeutic substance inlet, and configured to be opened and closed such that when the inlet valve is open there is fluid communication between the reservoir and the pump chamber and when the inlet valve is closed there is no fluid communication between the reservoir and the pump chamber, and (b) an outlet valve coupled to the therapeutic substance outlet, and configured to be opened and closed such that when the outlet valve is open there is fluid communication between the pump chamber and the subject and when the outlet valve is closed there is no fluid communication between the pump chamber and the subject, and the control circuitry is configured to:

(a) during the first pumping phase, open the inlet valve, close the outlet valve, and drive the plunger to draw the therapeutic substance into the pump chamber, and subsequently (b) during the second pumping phase, close the inlet valve, open the u e valve, and drive the plunger to deliver the therapeutic substance from the pump chamber in a plurality of discrete motions of the plunger.

For some applications, the inlet valve is a bidirectional valve, and the outlet valve is a unidirectional valve.

For some applications:

the control circuitry is configured to provide a valve-check phase in which the inlet valve and the outlet valve are closed, and to drive the plunger during the valve-check phase to advance in the pump chamber, and the apparatus further includes a pressure sensor disposed between the pump chamber and either one of the inlet valve and the outlet valve, and configured to measure a change in pressure inside the pump chamber as the plunger advances in the pump chamber during the valve-check phase.

For some applications, the control circuitry is configured to provide the valve-check phase between the first pumping phase and the second pumping phase.

For some applications, the control circuitry is configured to, during a negative-pressure reduction phase between the first pumping phase and the second pumping phase, maintain the inlet valve open and the outlet valve closed following the drawing of the therapeutic substance into the pump chamber.

For some applications, the control circuitry is configured to reduce an amplitude of negative pressure in the pump chamber by driving the plunger to push on the therapeutic substance in the pump chamber during the negative-pressure reduction phase.

For some applications, the control circuitry is configured not to drive the plunger to push on the therapeutic substance in the pump chamber during the negative-pressure reduction phase.

For some applications, a duration of the negative-pressure reduction phase is 0.1-5 seconds.

For some applications, a ratio of a duration of the negative-pressure reduction phase to a duration of the first pumping phase is between 1:10 and 5:1.

For some applications, the ratio of the duration of the negative-pressure reduction phase to the duration of the first pumping phase is between 1:10 and 1:1.

For some applications:

the therapeutic substance reservoir is configured to hold the therapeutic substance in a soluble solid state or a soluble gaseous state, the apparatus further includes a solvent reservoir configured to hold a solvent the soluble therapeutic substance, the pumping assembly is further shaped to define a mixing chamber having (a) a first mixing chamber inlet through which the therapeutic substance is received from the reservoir into the mixing chamber during the first pumping phase, and (b) a second mixing chamber inlet through which the solvent is received from the solvent reservoir into the mixing chamber during the first pumping phase, such that a therapeutic substance solution is formed within the mixing chamber, and the therapeutic substance inlet of the pump chamber is disposed between the mixing chamber and the pump chamber such that the therapeutic substance solution is received from the mixing chamber through the therapeutic substance inlet into the pump chamber during the first pumping phase.

For some applications:

the therapeutic substance reservoir is a first therapeutic substance reservoir and the therapeutic substance is a first therapeutic substance, the apparatus further includes a second therapeutic substance reservoir configured to hold a second therapeutic substance, and the pump chamber has a second therapeutic substance inlet through which the second therapeutic substance is received from the second reservoir into the pump chamber during the first pumping phase of the pumping assembly.

For some applications:

the pumping assembly is further shaped to define a mixing chamber having (a) a first mixing chamber inlet through which the first therapeutic substance is received from the first reservoir into the mixing chamber during the first pumping phase, and (b) a second mixing chamber inlet through which the second therapeutic substance is received from second reservoir into the mixing chamber during the first pumping phase, and the therapeutic substance inlet of the pump chamber is disposed between the mixing chamber and the pump chamber such that a mixture of the first and second therapeutic substances is received from the mixing chamber through the therapeutic substance inlet into the pump chamber during the first pumping phase.

For some applications:

the first therapeutic substance reservoir is configured to hold the first therapeutic substance in a soluble solid state or a soluble gaseous state, the apparatus further includes a solvent reservoir configured to hold a solvent for the first therapeutic substance, the pumping assembly is further shaped to define a mixing chamber having (a) a first mixing chamber inlet through which the soluble therapeutic substance is received from the first reservoir into the mixing chamber during the first pumping phase, and (b) a second mixing chamber inlet through which the solvent is received from the solvent reservoir into the mixing chamber during the first pumping phase such that a therapeutic substance solution is formed within the mixing chamber, and the therapeutic substance inlet of the pump chamber is a first therapeutic substance inlet valve through which the therapeutic substance solution is received from the mixing chamber into the pump chamber during the first pumping phase, the pump chamber further having a second therapeutic substance inlet valve through which the second therapeutic substance is received from the second, reservoir into the pump chamber during the first pumping phase.

There is further provided, in accordance with some applications of the present invention, a method of delivering a therapeutic substance to a subject, the method including:

using a plunger to draw the therapeutic substance front a therapeutic substance reservoir into a pump chamber of an electromechanical pumping assembly during a first pumping phase, the plunger being disposed such that therapeutic substance in the pump chamber is in direct contact with the plunger, and the pump chamber being in fluid communication with the reservoir and not in fluid communication with the subject during the first pumping phase; and subsequently, delivering the therapeutic substance from the pump chamber to the subject in a plurality of discrete dosages by delivering the therapeutic substance from the pump chamber in a plurality of discrete motions of the plunger during a second pumping phase, the pump chamber being in fluid communication with the subject and not in fluid communication with the reservoir during the second pumping phase.

For some applications:

(a) using the plunger to draw the therapeutic substance from the therapeutic substance reservoir into the pump chamber includes (i) opening an inlet valve disposed in a therapeutic substance inlet of the pump chamber, through which the therapeutic substance is received from the reservoir into the pump chamber during the first pumping phase, and (ii) closing an outlet valve disposed in a therapeutic substance outlet of the pump chamber, through which the therapeutic substance is delivered from the pump chamber to the subject during the second pumping phase, and (b) delivering the therapeutic substance from the pump chamber to the subject includes closing the inlet valve and opening the outlet valve.

For some applications, the method further includes reducing an amplitude of negative pressure in the pump chamber during a negative-pressure reduction phase between the first pumping phase and the second pumping phase, by maintaining the pump chamber in fluid communication with the reservoir and not in fluid communication with the subject following the drawing of the therapeutic substance into the pump chamber.

For some applications, using the plunger to draw the therapeutic substance from the therapeutic substance reservoir into the pump chamber includes using the plunger to draw the therapeutic substance from the therapeutic substance reservoir into the pump chamber in a single motion of the plunger.

For some applications, using the plunger to draw the therapeutic substance from the therapeutic substance reservoir into the pump chamber includes using the plunger to draw the therapeutic substance from the therapeutic substance reservoir into the pump chamber in one or more discrete expansion motions of the plunger, wherein each expansion motion is longer in duration than any one of the plurality of discrete motions of the plunger during the second pumping phase.

There is further provided, in accordance with some applications of the present invention, apparatus for delivering a therapeutic substance to a subject, the apparatus including:

a therapeutic substance reservoir configured to hold a therapeutic substance; and an electromechanical pumping assembly coupled to the reservoir, the pumping, assembly shaped to define a pump chamber having:

(a) a therapeutic substance inlet through which the therapeutic substance is received from the reservoir into the pump chamber during a first pumping phase of the pumping assembly, (b) a therapeutic substance outlet through which the therapeutic substance is delivered from the pump chamber to the subject during a second pumping phase of the pumping assembly, the pumping assembly including:

a plunger disposed such that therapeutic substance in the pump chamber is in direct contact with the plunger;

a cam coupled to the plunger, such that as the cam rotates it drives the plunger to deliver the therapeutic substance from the pump chamber;

a toothed wheel coupled to the cam and configured to drive the cam to rotate in a plurality of discrete motions of the cam, each discrete motion of the cam corresponding to a discrete rotational motion of the toothed wheel; and a moving-coil motor coupled to the toothed wheel such that a discrete movement of the coil causes one discrete rotational motion of the toothed wheel.

For some applications, the apparatus further includes a lever arm coupled to the moving-coil motor and the toothed wheel, and configured to translate the discrete movement of the coil into the discrete rotational motion of the toothed wheel.

The present invention will be more fully understood from the following detailed description of applications thereof, taken together with the drawings, in which:

DETAILED DESCRIPTION

Figure 1:
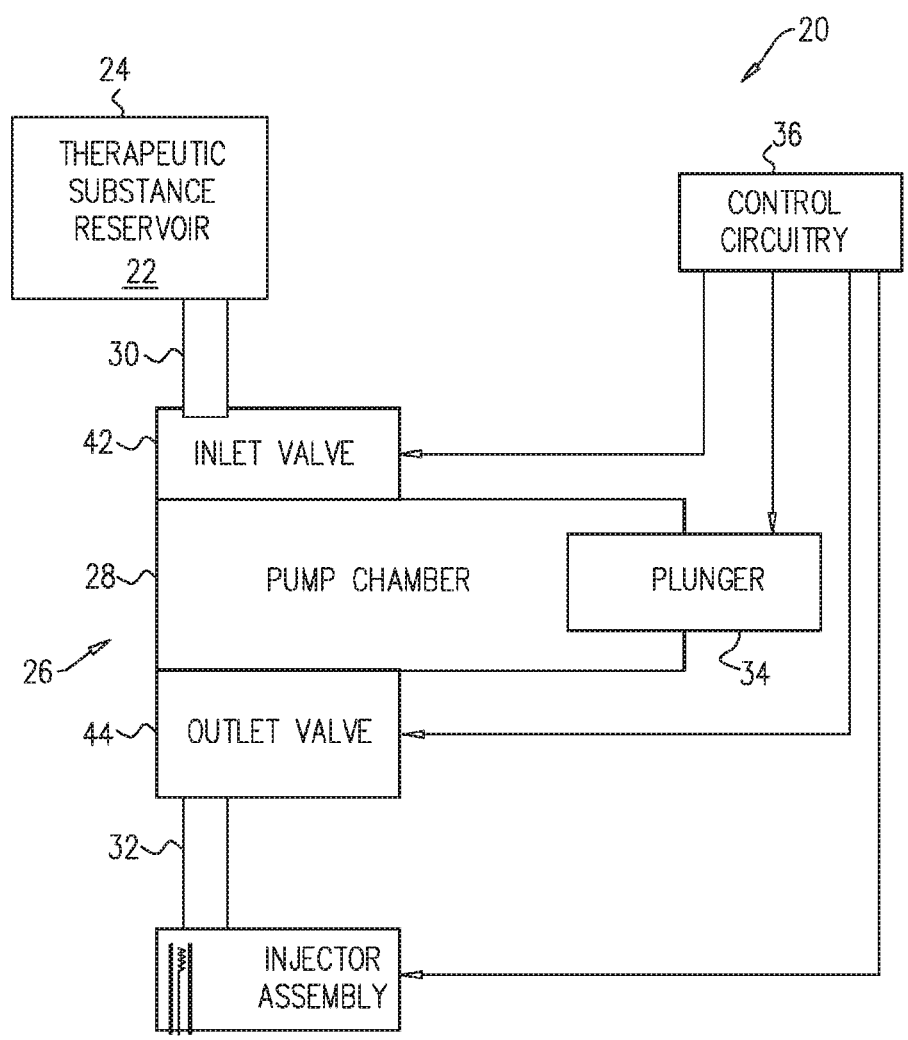
FIG. 1 is a block diagram showing a therapeutic substance reservoir coupled to an electromechanical pumping assembly for delivering a therapeutic substance to a subject, in accordance with some applications of the present invention.

Reference is now made to FIG. 1, which is a block diagram showing a therapeutic substance reservoir coupled to an electromechanical pumping assembly for delivering a 111 therapeutic substance to a subject, in accordance with some applications of the present invention. Apparatus 20 is an apparatus for delivering a therapeutic substance 22 to a subject, such as a wearable medical pump, e.g., a patch pump. A therapeutic substance reservoir 24 is configured to hold therapeutic substance 22. Apparatus 20 may come with reservoir 24 prefilled by a medical vendor or device manufacturer, or reservoir 24 may be filled by the user or a physician prior to use of the wearable pump. Alternatively, reservoir 24 may come prefilled from a medical vendor ready to be loaded or inserted into apparatus 20 prior to use. Typically, therapeutic substance reservoir 24 holds a volume of therapeutic substance 22 of at least 1 ml and/or less than 10 ml. For some applications, therapeutic substance reservoir 24 may be a bag, a cartridge, or a syringe.

When apparatus 20 is assembled and ready for use, an electromechanical pumping assembly 26 is coupled to therapeutic substance reservoir 24. Electromechanical pumping assembly 26 is shaped to define a rigid pump chamber 28 that has (a) a therapeutic substance inlet 30, through which therapeutic substance 22 is received from reservoir 24 into pump chamber 28, and (b) a therapeutic substance outlet 32, through which therapeutic substance 22 is delivered from pump chamber 28 to the subject. For some applications, pump chamber 28 may hold a volume of therapeutic substance 22 of at least 5 microliters and/or less than 100 microliters.

Figure 3:
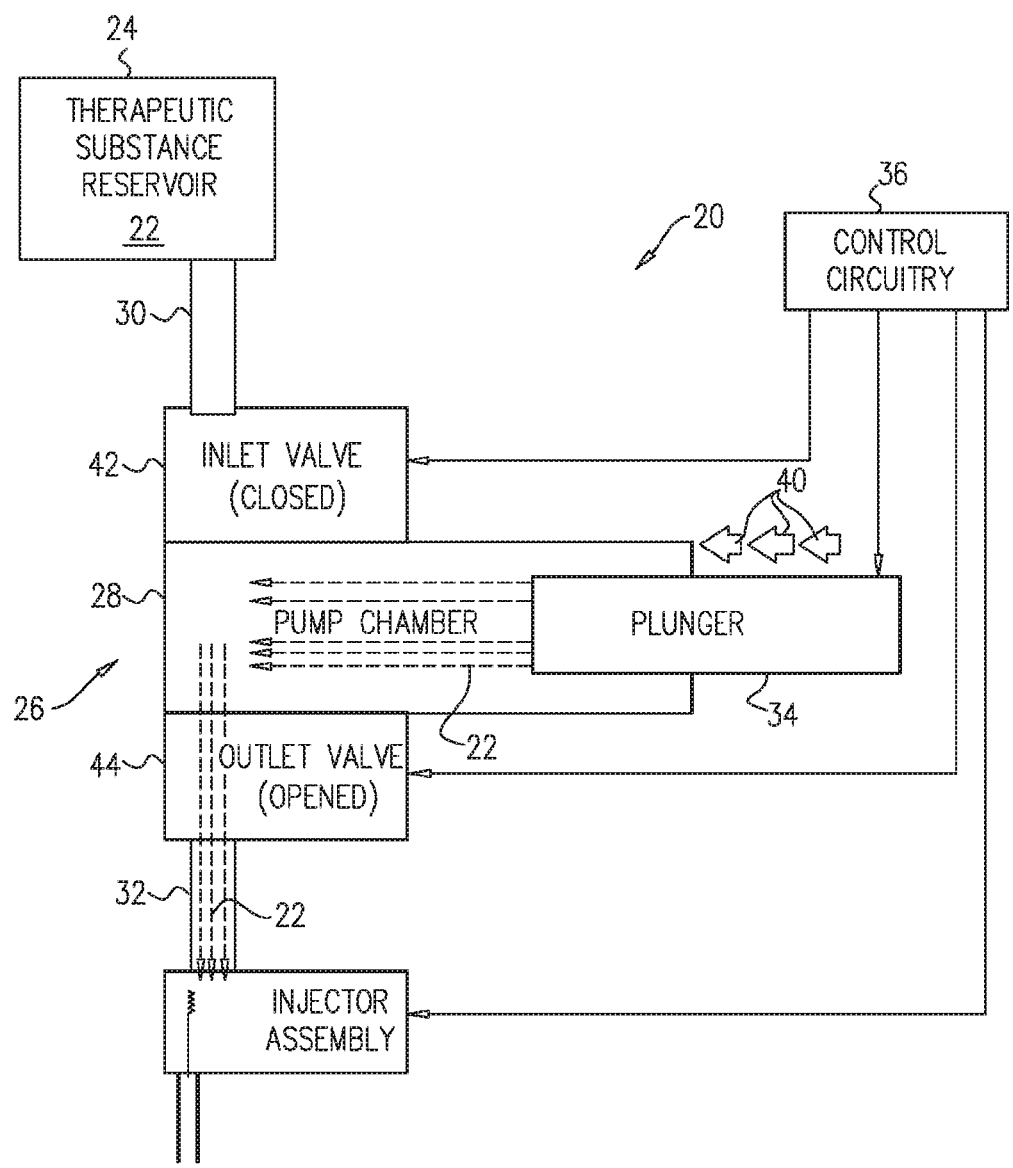
FIG. 3 is a block diagram showing a second pumping phase of the electromechanical pumping assembly, in accordance with some applications of the present invention.
Figure 4:
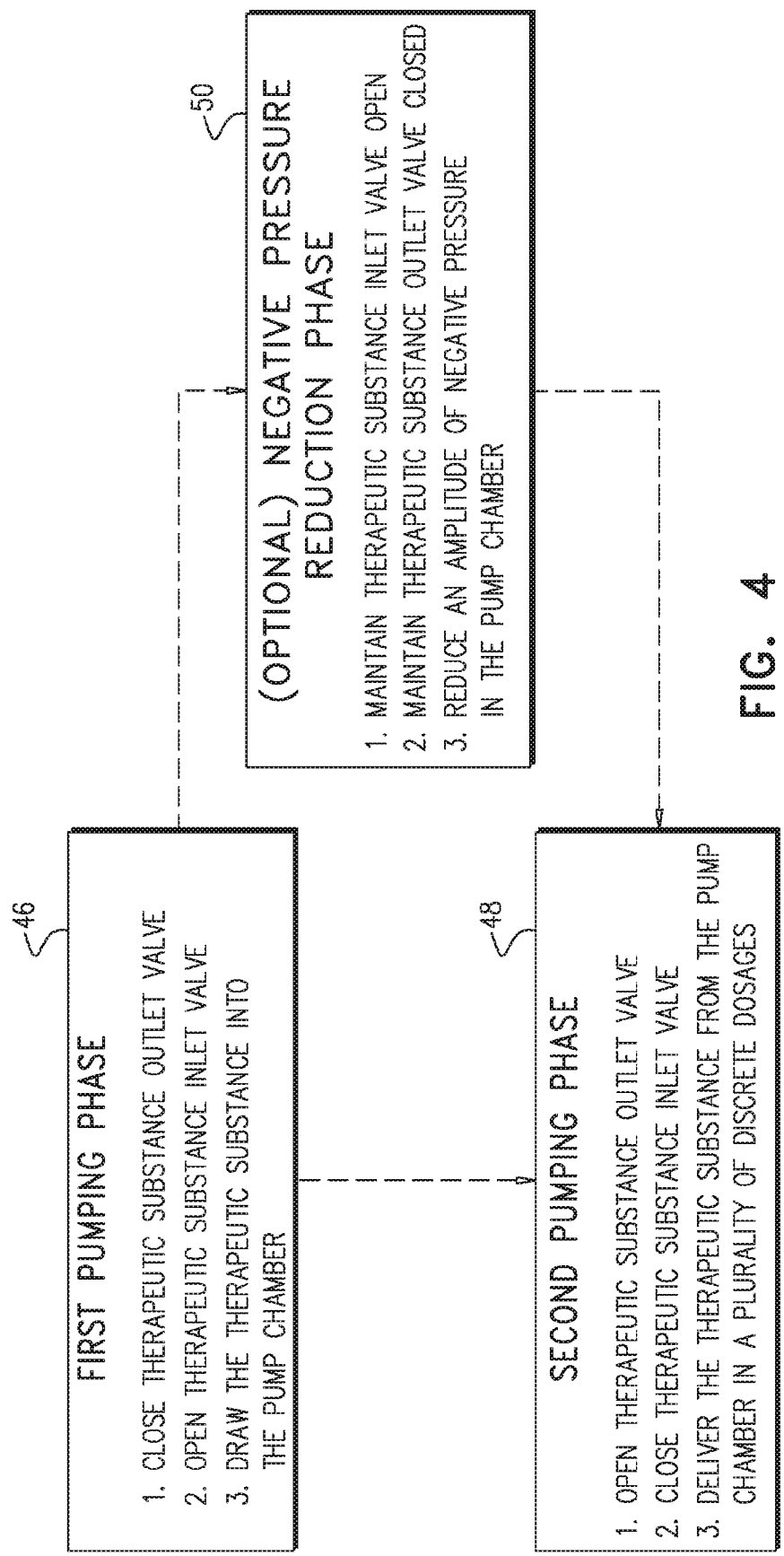
FIG. 4 is a flow chart showing a method of delivering the therapeutic substance to the subject, in accordance with some applications of the present invention.
Figure 5:
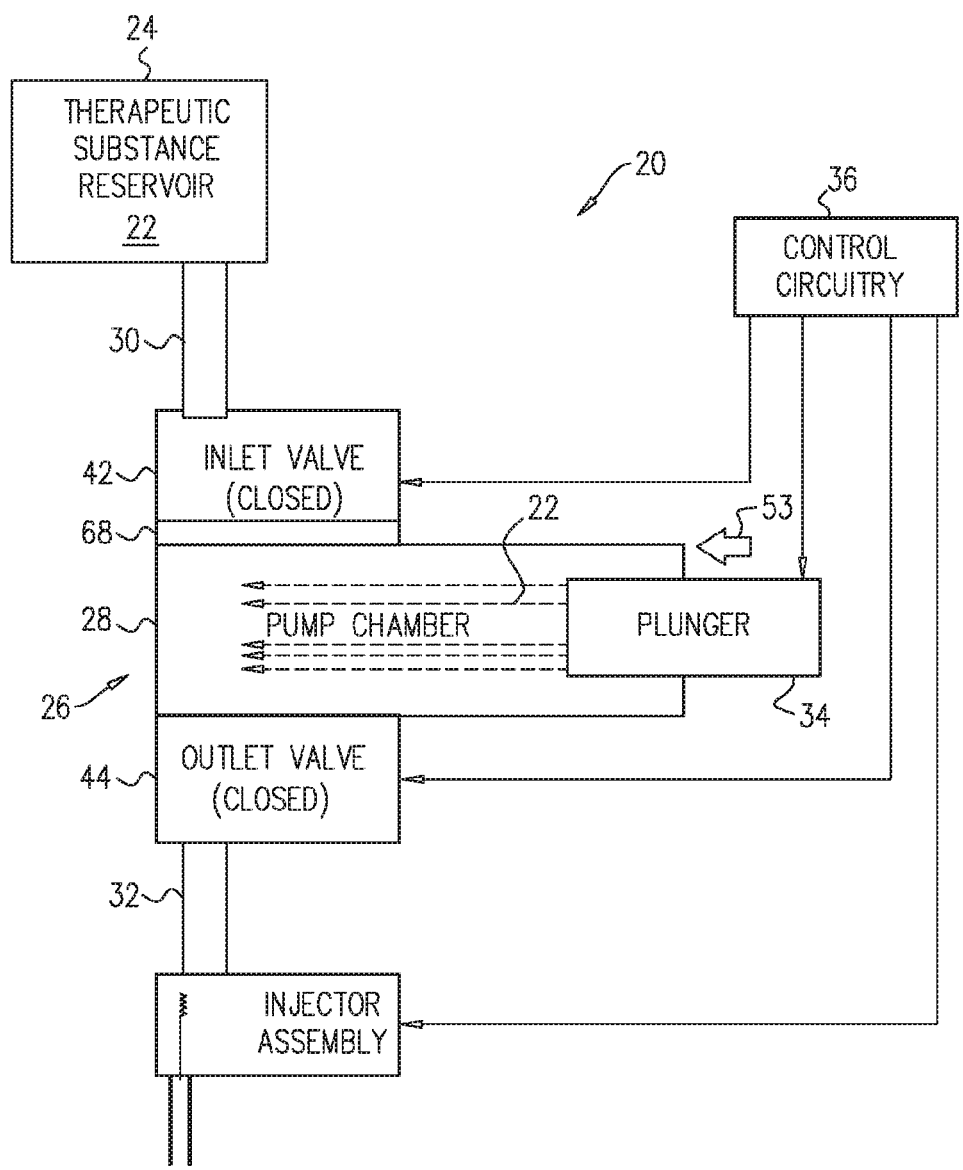
FIG. 5 is a block diagram showing a valve-check phase of the electromechanical pumping assembly, in accordance with some applications of the present invention.

A plunger 34 is disposed in apparatus 20 such that therapeutic substance 22 in pumping chamber 28 is in direct contact with plunger 34 (such as is shown in FIGS. 3-5), e.g., slidably disposed within pump chamber 28 while sealably contacting the inside of pump chamber 28. Pump chamber 28 being both small and rigid enables high accuracy in the volume of therapeutic substance 22 being delivered to the subject when plunger 34 pushes on therapeutic substance 22 in pump chamber 28. Even a small amount of movement of plunger 34, e.g., 0.1 mm, will have a significant and accurate effect on the volume of therapeutic substance 22 delivered from pump chamber 28 to the subject.

Figure 2:
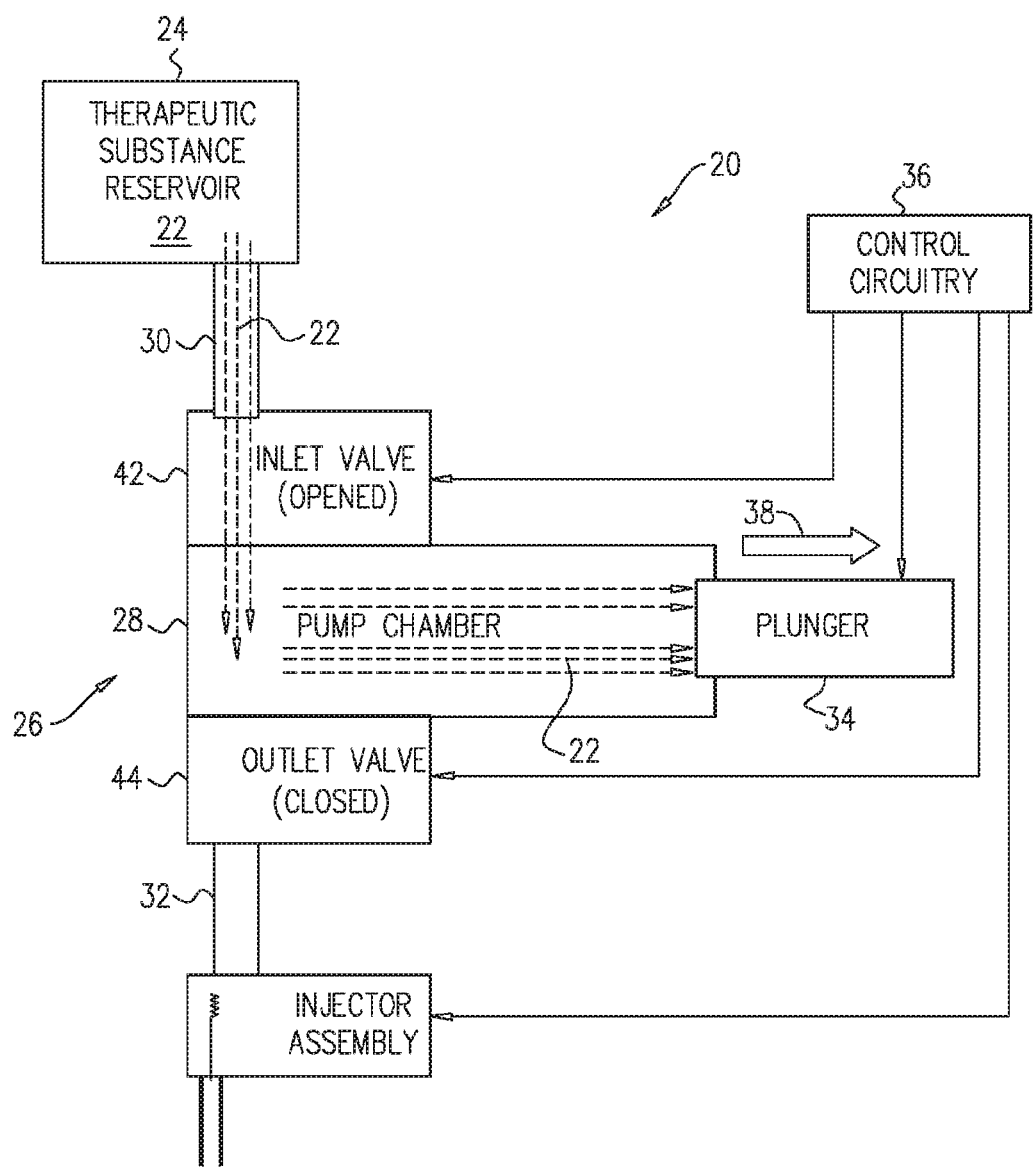
FIG. 2 is a block diagram showing a first pumping phase of the electromechanical pumping assembly, in accordance with some applications of the present invention.

Reference is now made to FIGS. 2-3, which are block diagrams showing different pumping phases of electromechanical pumping assembly 26, For some applications, electromechanical pumping assembly 26 is driven to operate in two pumping phases by control circuitry 36. In a first pumping phase (FIG. 2), control circuitry 36 is configured to drive plunger 34 to draw therapeutic substance 22 into pump chamber 28. Arrow 38 in FIG. 2 is representative of the motion of plunger 34 as it draws therapeutic substance 22 into pump chamber 28. In a second pumping phase (FIG. 3), control circuitry 36 is configured to drive plunger 34 to deliver therapeutic substance 22 from pump chamber 28 to the subject in a plurality of discrete motions of plunger 34. Arrows 40 in FIG. 3 are representative of the plurality of discrete motions of plunger 34 as therapeutic substance 22 is delivered to the subject. The number of arrows 40 shown in FIG. 3 is not indicative of the number of discrete motions of plunger 34, rather arrows 40 are simply a visualization of separate discrete motions. Delivery of therapeutic substance 22 using a plurality of discrete motions of plunger 34 allows the volume of therapeutic substance 22 inside pump chamber 28 to be delivered to the subject in a plurality of precise and controlled dosages. Typically, respective durations of the plurality of discrete motions of plunger 34 during the second pumping phase are equal.

For some applications, control circuitry 36 is configured to drive plunger 34 to draw therapeutic substance 22 into pump chamber 28 in a single motion of plunger 34, e.g., plunger 34 is pulled back in a single motion to draw a volume of therapeutic substance 22 into pump chamber 28 during the first pumping phase. Alternatively, control circuitry 36 may be configured to drive plunger 34 to draw therapeutic substance 22 into pump chamber 28 in one or more discrete expansion motions of plunger 34, e.g., plunger 34 may be pulled half way out in one motion and then the rest of the way out in a second separate motion. In this case, a duration of some or all expansion motions of plunger 34 during the first pumping phase are typically longer than a duration of any one of the plurality of discrete motions of plunger 34 during the second pumping phase.

For some applications, control circuitry 36 drives plunger 34 such that a duration of the first pumping phase and a duration of the second pumping phase are unequal. For example, a duration of the second pumping phase may be at least 10 times, e.g., 30 times, e.g., 50 times, longer than a duration of the first pumping phase. For some applications, a duration of the second pumping phase is at least 5 and/or less than 50 times longer than a duration of the first pumping phase.

Typically, the direction of flow of the therapeutic substance 22 within electromechanical pumping assembly 26 is controlled by a set of valves. An inlet valve 42 is coupled to therapeutic substance inlet 30, and configured to be opened and closed such that when inlet valve 42 is open there is fluid communication between reservoir 24 and pump chamber 28, and when inlet valve 42 is closed there is no fluid communication between reservoir 24 and pump chamber 28. An outlet valve 44 is coupled to therapeutic substance outlet 32 and configured to be opened and closed such that when outlet valve 44 is open there is fluid communication between pump chamber 28 and the subject, and when outlet valve 44 is closed there is no fluid communication between pump chamber 28 and the subject.

During the first pumping phase, control circuitry 36 is configured to open inlet valve 42, close outlet valve 44 and drive plunger 34 to draw therapeutic substance 22 from reservoir 24 into pump chamber 28, e.g., control circuitry 36 sets inlet valve 42 and outlet valve 44 such that therapeutic substance 22 can flow only between reservoir 24 and pump chamber 28. Thus, as plunger 34 is drawn hack, therapeutic substance 22 is drawn into pump chamber 28. Subsequently, during the second pumping phase, control circuitry 36 is configured to close inlet valve 42, open outlet valve 44 and drive plunger 34 to deliver therapeutic substance 22 from pump chamber 28 in a plurality of discrete motions of plunger 34. For example, control circuitry 36 may set inlet valve 42 and outlet valve 44 such that therapeutic substance 22 can flow only between pump chamber 28 and the subject, and plunger 34 is incrementally pushed back into pump chamber 28 in a plurality of discrete motions thereby delivering therapeutic substance 22 to the subject in a plurality of discrete dosages.

Reference is now made to FIG. 4, which is a flow chart showing the method described herein of delivering therapeutic substance to the subject, in accordance with some applications of the present invention. Steps 46 and 48 show the first and second pumping phases, respectively, as described hereinabove with reference to FIGS. 2-3. Step 50 shows an optional negative-pressure reduction phase between the first and second pumping phase, further described hereinbelow with reference to FIG. 6.

Reference is now made to FIG. 5, which is a block diagram showing a valve-check phase of electromechanical pumping assembly 26, in accordance with some applications of the present invention. Inlet valve 42 and outlet valve 44 can be checked to ensure that there are no leaks during a valve-check phase. For some applications, following the drawing of therapeutic substance 22 into pump chamber 28, control circuitry 36 is configured to close both inlet valve 42 and outlet valve 44 and to drive plunger 34 to slightly push on therapeutic substance 22 inside pump chamber 28. Arrow 53 in FIG. 5 is representative of slight motion of plunger 34 back into pump chamber 28 during the valve-check phase. Pressure sensor 68 is typically disposed between pump chamber 28 and either one of inlet valve 42 and outlet valve 44, and is configured to measure a change in pressure when plunger 34 pushes on therapeutic substance 22 during the valve-check phase. If pressure sensor 68 senses an expected increase in pressure during the valve-check phase then inlet valve 42 and outlet valve 44 are working as expected. If pressure sensor 68 senses an increase in pressure that is lower than the expected value during the valve-check phase it may be an indication that some degasification has occurred within pump chamber 28, resulting in (compressible) air bubbles forming within therapeutic substance 22. If pressure sensor 68 does not sense any increase in pressure during the valve-check phase, it is an indication that at least one of the valves may leak. For some applications, the valve-check phase may occur prior to a first use of apparatus 20. Alternatively or additionally, the valve-check phase may be provided by apparatus 20 between the first pumping phase and the second pumping phase.

Figure 6:
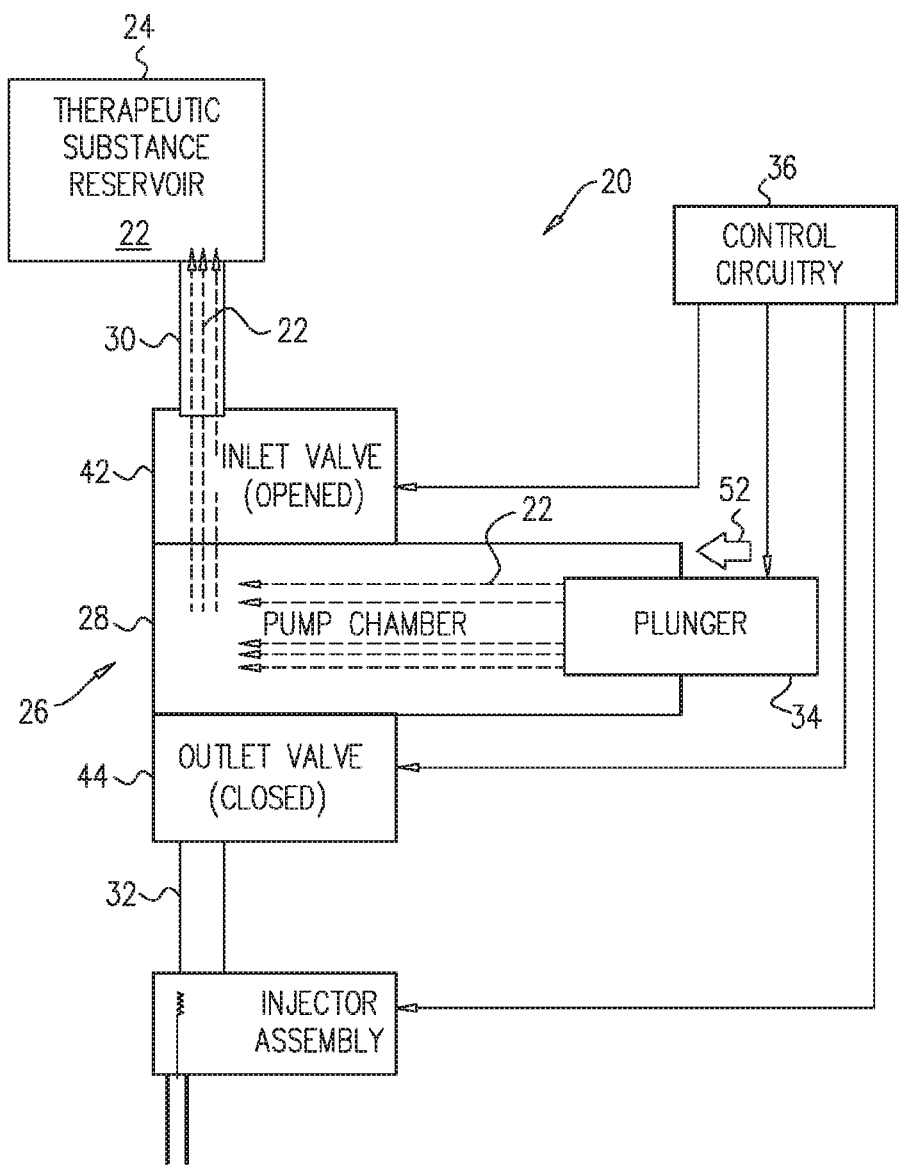
FIG. 6 is a block diagram showing a negative-pressure reduction phase of the electromechanical pumping assembly, in accordance with some applications of the present invention.

Reference is now made to FIG. 6, which is a block diagram showing the negative-pressure reduction phase shown in FIG. 4, in accordance with some applications of the present invention. When therapeutic substance 22 is drawn into pumping chamber 28, negative pressure may build up inside pump chamber 28 possibly causing degassing of dissolved gas, e.g., formation of air bubbles, inside therapeutic substance 22. For some applications, the negative-pressure reduction phase provided by the apparatus between the first and second pumping phase may reduce an amplitude of negative pressure in pump chamber 28. During the negative-pressure reduction phase, circuitry 36 is configured to maintain inlet valve 42 open and outlet valve 44 closed, i.e., maintain pump chamber 28 in fluid communication with reservoir 24 and not in fluid communication with the subject, following the drawing of therapeutic substance 22 into pump chamber 28.

For some applications, during the negative-pressure reduction phase, control circuitry 36 is configured to further reduce the amplitude of negative pressure in pump chamber 28 by driving plunger 34 to push on therapeutic substance 22 in pump chamber 28, causing some of therapeutic substance 22 to flow back into reservoir 24 through open inlet valve 42. Alternatively, control circuitry 36 may be configured not to actively drive plunger 34 to push on therapeutic substance 22, but rather the amplitude of negative pressure in pump chamber 28 may be reduced by plunger 34 naturally being sucked back into pump chamber 28 by the negative pressure, causing some of therapeutic substance 22 to flow back into reservoir 24 through open inlet valve 42. Arrow 52 in FIG. 6 is representative of the slight motion of plunger 34 back into pump chamber 28 during the negative-pressure reduction phase. For some applications, inlet valve 42 is a bidirectional valve to accommodate therapeutic substance 22 flowing back into reservoir 24 during the negative-pressure reduction phase, and outlet valve 44 is a unidirectional valve to ensure no therapeutic substance flows back into pump chamber 28 after being pushed through outlet valve 44. For some applications, inlet valve 42 and outlet valve 44 are both bidirectional, and the direction of flow through the valves when they are open is determined by relative pressures on either side of the valve.

For some applications, a duration of the negative-pressure reduction phase may range from 10 times shorter than the duration of the first pumping phase to 5 times longer than the duration of the first pumping phase. Typically, the negative-pressure reduction phase is shorter than the first pumping phase, i.e., the duration of the negative-pressure reduction phase ranges from 10 times shorter than the duration of the first pumping phase to substantially equal to the duration of the first pumping phase. For example, the duration of the negative-pressure reduction phase may be 0.1-5 seconds.

Figure 7:
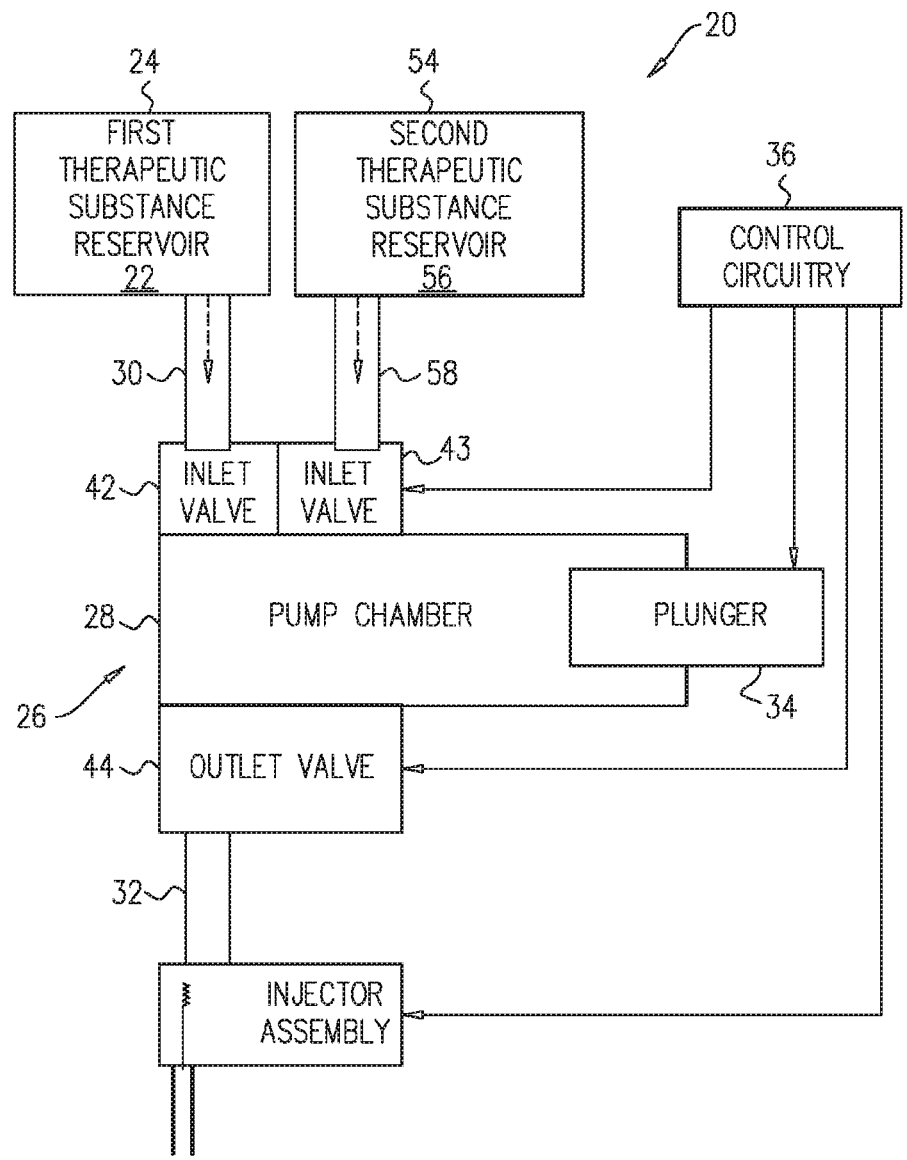
FIG. 7 is a block diagram showing multiple therapeutic substance reservoirs coupled to the electromechanical pumping assembly, in accordance with some applications of the present invention.

Reference is now made to FIG. 7, which is a block diagram showing multiple therapeutic substance reservoirs coupled to electromechanical pumping assembly 26, in accordance with some applications of the present invention. For some applications, apparatus 20 may have a second therapeutic substance reservoir 54, which holds a second therapeutic substance 56. Pump chamber 28 has a second therapeutic substance inlet 58 through which second therapeutic substance 56 is received from second reservoir 54 into pump chamber 28 during the first pumping phase. Each of the two therapeutic substances may be delivered at different tunes through pump chamber 28, or they may be drawn together into pump chamber 28 and delivered concurrently. A second therapeutic substance inlet valve 43 is coupled to second therapeutic substance inlet 58 and configured to be opened and closed such that when second inlet valve 43 is open there is fluid communication between second reservoir 54 and pump chamber 28.

Figure 8:
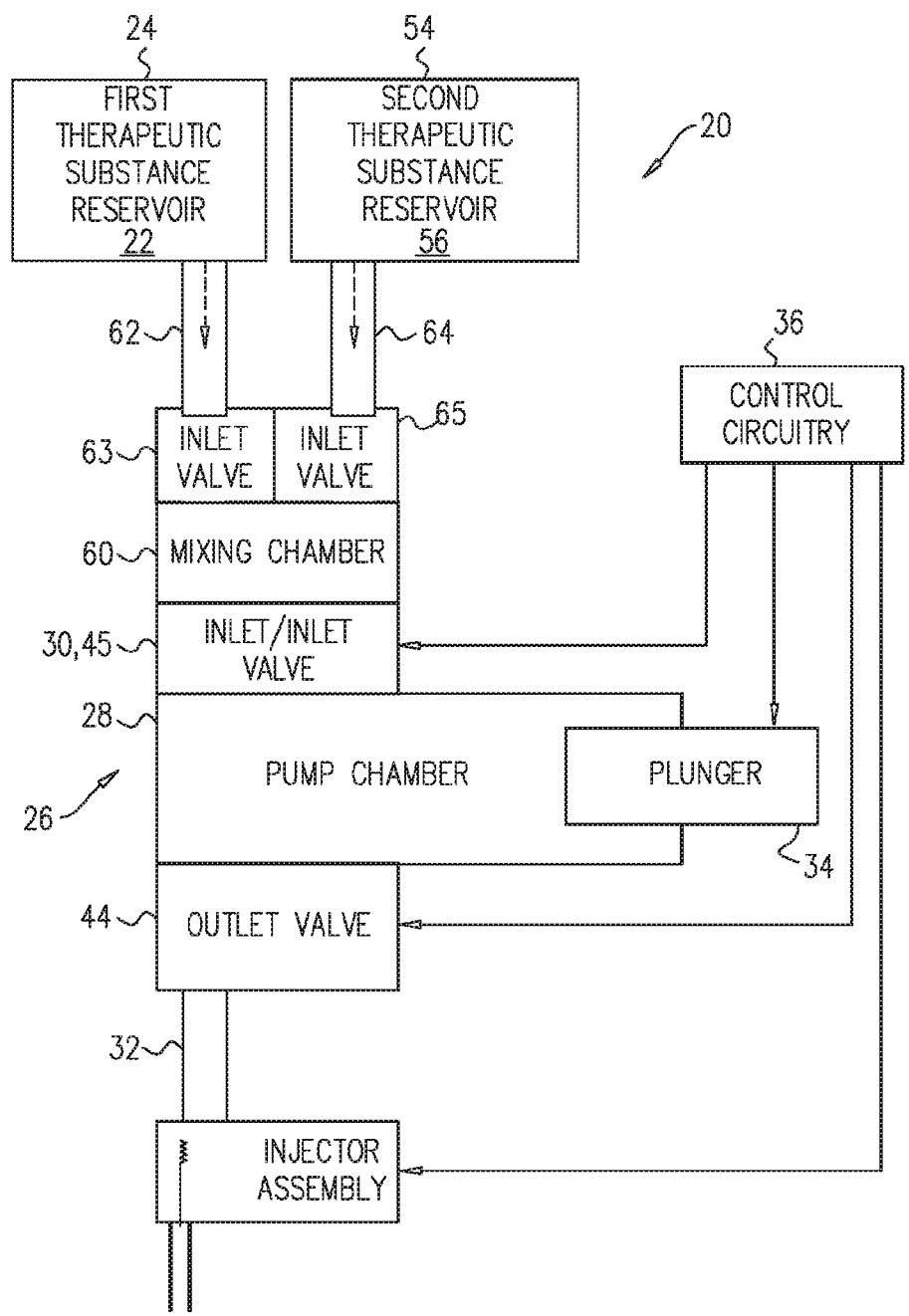
FIG. 8 is a block diagram showing multiple therapeutic substance reservoirs coupled to the electromechanical pumping assembly, and a mixing chamber for the therapeutic substances, in accordance with some applications of the present invention.

Reference is now made to FIG. 8, which is a block diagram showing first and second therapeutic substance reservoirs 24 and 56, respectively, coupled to electromechanical pumping assembly 26, and a mixing chamber 60 for the therapeutic substances, in accordance with some applications of the present invention. For some applications, mixing chamber 60 provides a space for the first and second therapeutic substances to properly mix together before entering pump chamber 28, Mixing chamber 60 has (a) a first mixing chamber inlet 62 through which the first therapeutic substance is received from first reservoir 24 into mixing chamber 60 during the first pumping phase, and (b) a second mixing chamber inlet 64 through which the second therapeutic substance is received from second reservoir 54 into mixing chamber 60 during the first pumping phase A first mixing chamber valve 63 is coupled to first mixing chamber inlet 62 and configured to control fluid communication between first therapeutic substance reservoir 24 and mixing chamber 60, and a second mixing chamber valve 65 is coupled to second mixing chamber inlet 64 and configured to control fluid communication between second therapeutic substance reservoir 54 and mixing chamber 60. A mixture of the first and second therapeutic substances is received from mixing chamber 60 into pump chamber 28 during the first pumping phase. A pump chamber inlet valve 45 is disposed between mixing chamber 60 and pump chamber 28 and configured to control fluid communication between mixing chamber 60 and pump chamber 28.

Figure 9:
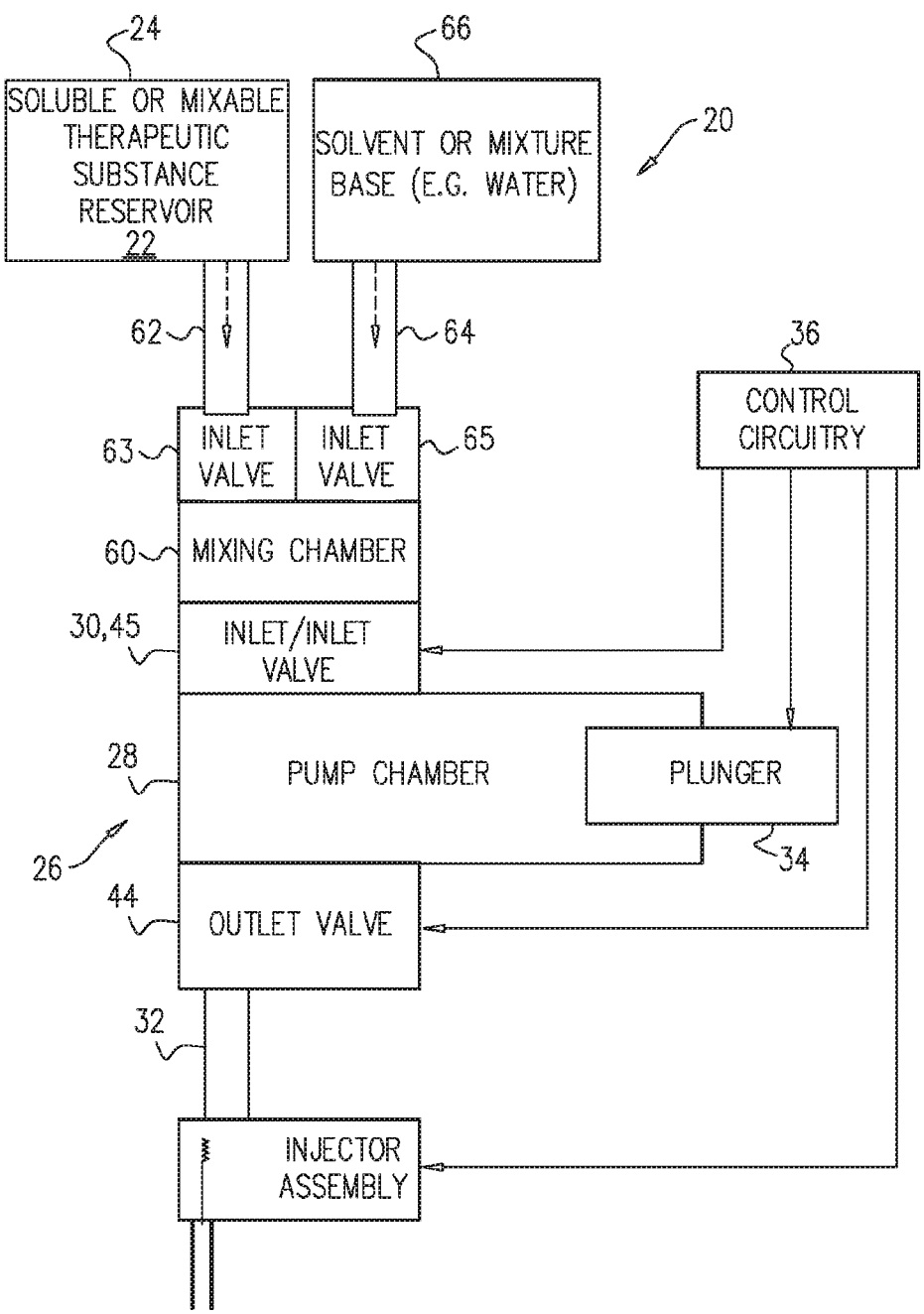
FIG. 9 is a block diagram showing a therapeutic substance reservoir and a solvent reservoir coupled to the electromechanical pumping assembly, and a mixing chamber for the formation of a therapeutic substance solution, in accordance with some applications of the present invention.

Reference is now made to FIG. 9, which is a block diagram showing therapeutic substance reservoir 24 and a solvent reservoir 66 coupled to electromechanical pumping assembly 26, and mixing chamber 60 for the formation of a therapeutic substance solution, in accordance with some applications of the present invention. For some applications, reservoir 24 is configured to hold therapeutic substance 22 in a soluble solid state or a soluble gaseous state. A solvent reservoir 66 holds a solvent for soluble therapeutic substance 22. During the first pumping phase, therapeutic substance 22 in its solid, e.g., powder, or gaseous state is received from reservoir 24 into mixing chamber 60 through first mixing chamber inlet 62, and the solvent is received from solvent reservoir 66 into mixing chamber 60 through second mixing chamber inlet 64, such that a therapeutic substance solution is formed within mixing chamber 60. The therapeutic substance solution is received from mixing chamber 60 into pump chamber 28 during the first pumping phase. First mixing chamber valve 63 is coupled to first mixing chamber inlet 62, second mixing chamber valve 65 is coupled to second mixing chamber inlet 64, and pump chamber inlet valve 45 is disposed between mixing chamber 60 and pump chamber 28 as described hereinabove with reference to FIG. 8.

Figure 10:
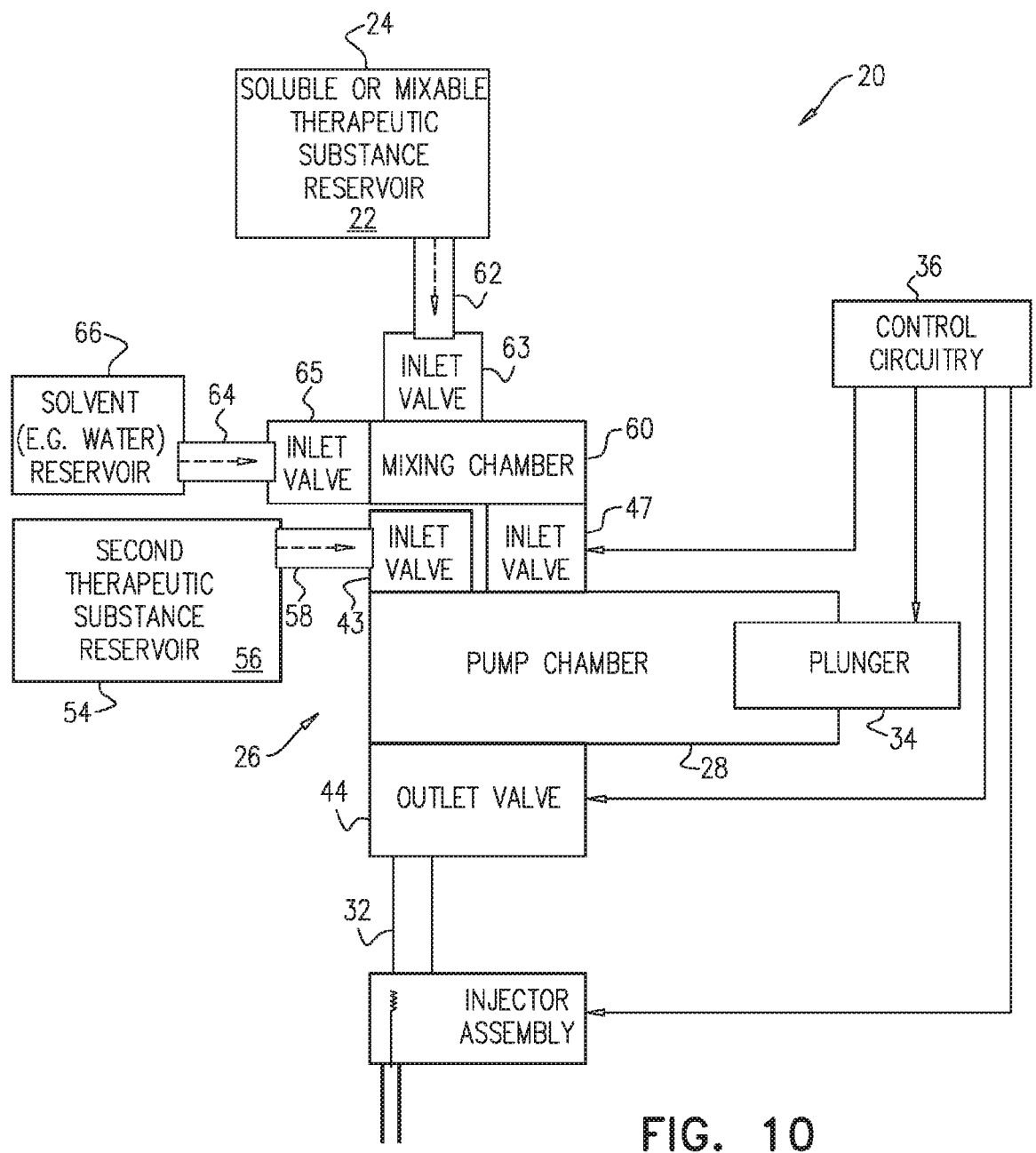
FIG. 10 is a block diagram showing multiple therapeutic substance reservoirs and a solvent reservoir coupled to the electromechanical pumping assembly, and a mixing chamber for the formation of a therapeutic substance solution, in accordance with some applications of the present invention.

Reference is now made to FIG. 10, which is a block diagram showing multiple; therapeutic substance reservoirs and solvent reservoir 66 coupled to electromechanical pumping assembly 26, and mixing chamber 60 for the formation of a therapeutic substance solution, in accordance with some applications of the present invention. Various features of the abovementioned configurations may be combined. For example, reservoir 24 may hold therapeutic substance 22 in a soluble solid or soluble gaseous state with a solvent disposed in solvent reservoir 66, such that a therapeutic substance solution is formed in mixing chamber 60, and apparatus 20 may have second reservoir 54 holding second therapeutic substance 56 as well. A pump chamber inlet valve 47 is disposed between mixing chamber 60 and pump chamber 28.

Figure 11A:
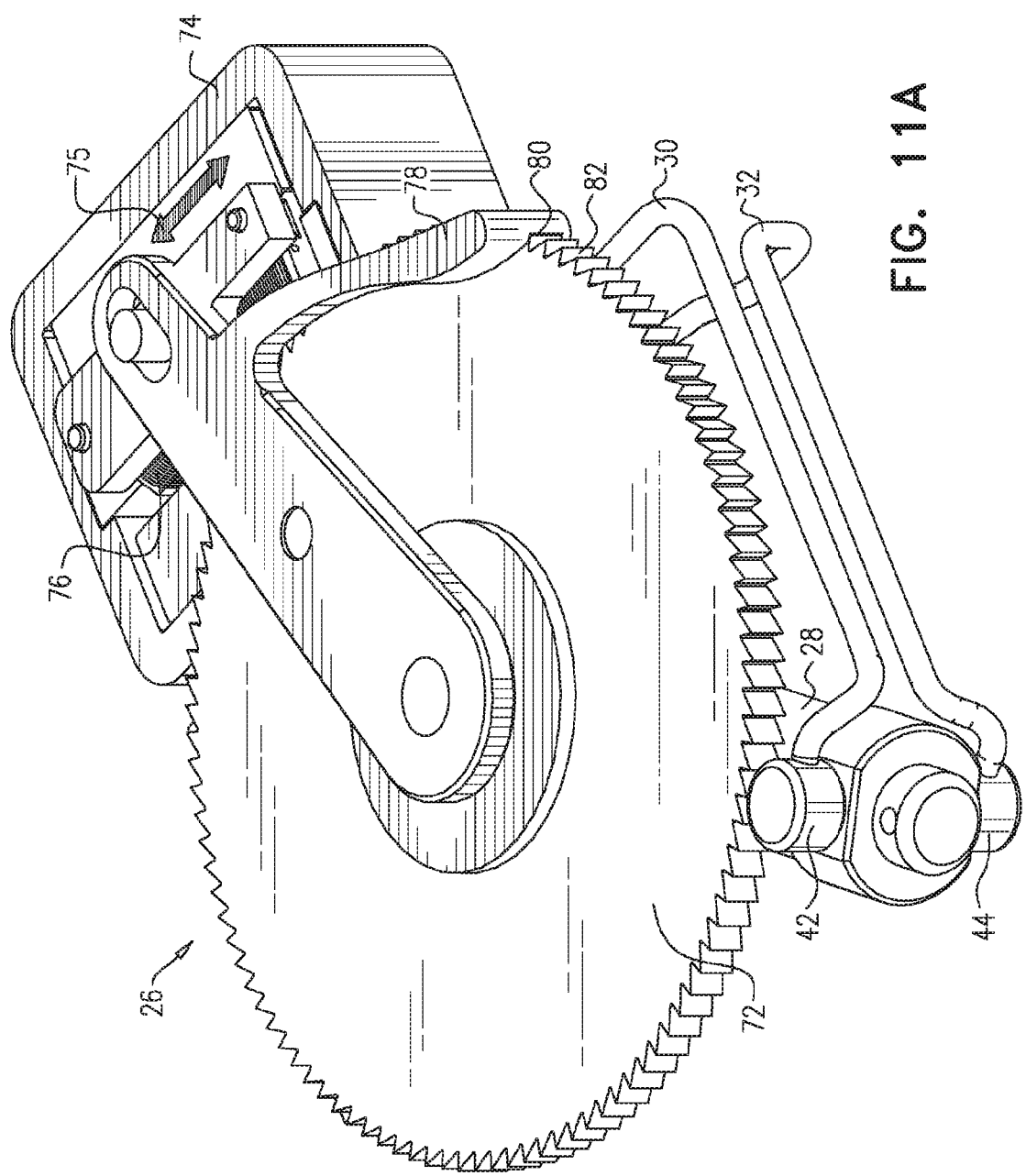
FIGS. 11A-B are schematic illustrations of the electromechanical pumping assembly showing a moving-coil motor, a toothed wheel, and a cam, in accordance with some applications of the present invention.
Figure 11B:
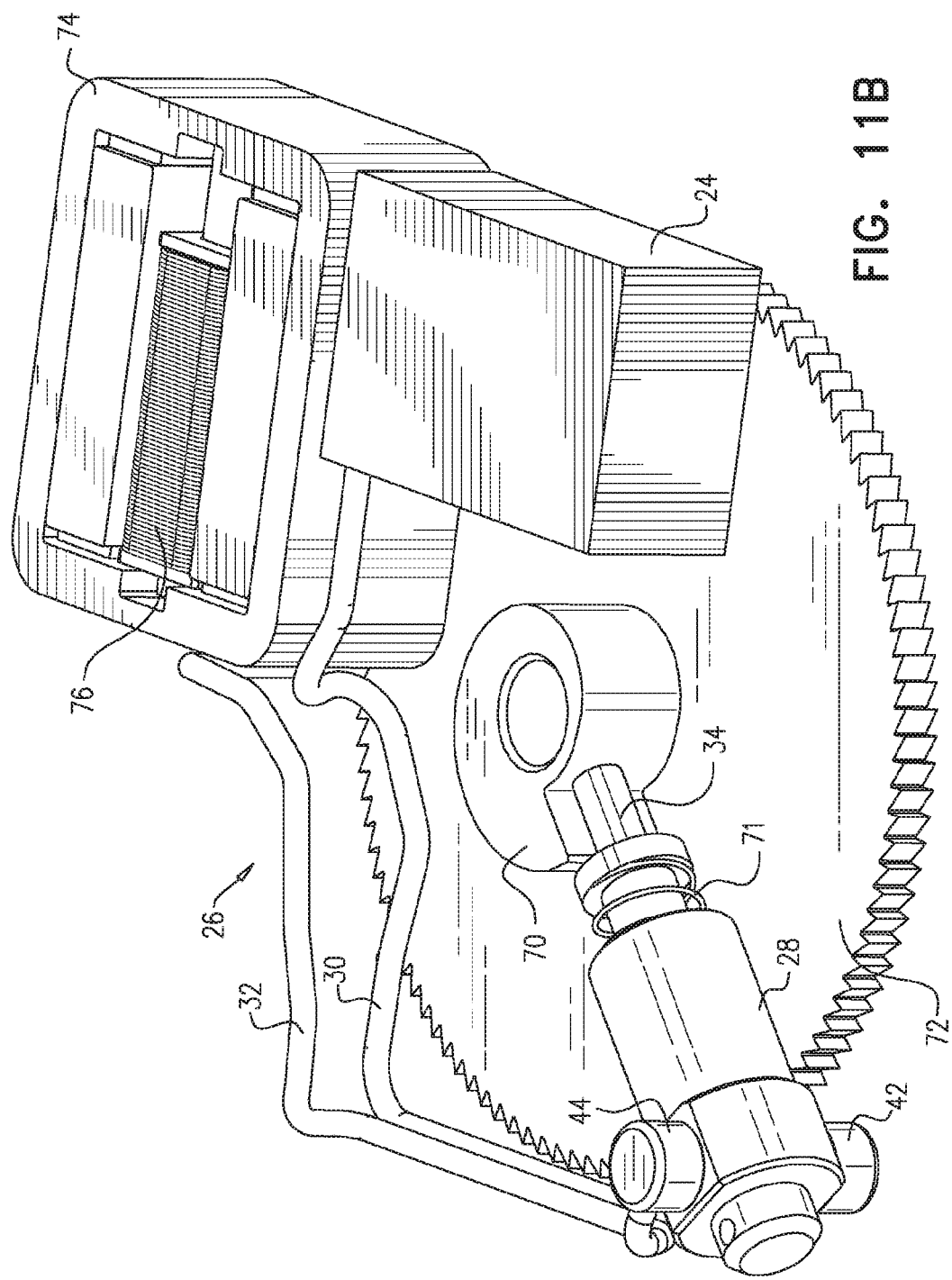

Reference is now made to FIGS. 11A-B, which are schematic illustrations of electromechanical pumping assembly 26 showing a moving-coil motor, a toothed wheel, and a cam, in accordance with some applications of the present invention. A cam 70 is coupled to plunger 34 such that as cam 70 rotates (clockwise in FIG. 11B) it drives plunger 34 to deliver therapeutic substance 22 from pump chamber 28 to the subject. For example, cam 70 may cause plunger 34 to advance within pump chamber 28 as it rotates. For some applications, plunger 34 may be coupled to a deformed elastic element, e.g., a compressed spring 71, that drives plunger 34 to draw therapeutic substance 22 into pump chamber 28 as spring 71 returns toward its resting state. Cam 70 subsequently drives plunger 34 to advance within pump chamber 28 as it rotates, thereby compressing spring 71. Cam 70 may be shaped so that at a predetermined angle of rotation, corresponding to plunger 34 having delivered a desired amount (e.g., all) of therapeutic substance 22 in pump chamber 28, plunger 34 is released and spring 71 is allowed to drive plunger 34 to draw therapeutic substance 22 into pump chamber 28.

Driving the rotation of cam 70 is a toothed wheel 72 that is driven to rotate through a plurality of discrete rotational motions by a moving-coil motor 74. Toothed wheel 72 is coupled to cam 70 and configured to rotate cam 70 in a plurality of discrete motions of cam 70, each discrete motion of cam 70 corresponding to a discrete rotational motion of the toothed wheel. Moving-coil motor 74 operates such that as current is applied to a coil 76 of moving-coil motor 74, coil 76 undergoes a discrete motion in a first direction. Applying an opposite current to coil 76 causes another discrete motion of coil 76 in a second direction opposite the first discrete motion. Therefore, alternating the current applied to coil 76 causes coil 76 to undergo alternating discrete motions, e.g., to move linearly back and forth. Arrow 75 in FIG. 11A represents the back and forth motion of coil 76. Moving-coil motor 74 is coupled to toothed wheel 72 such that a discrete movement of coil 76 causes a discrete rotational motion of toothed wheel 72, which in turn causes one discrete motion of cam 70, which in turn causes one discrete motion of plunger 34.

For example, a lever arm 78 may be coupled to moving-coil motor 74 and toothed wheel 72 such that as coil 76 undergoes a discrete movement, lever arm 78 pulls on a tooth 80 of toothed wheel 72 so as to rotate toothed wheel 72 through one discrete rotational motion. As the current is reversed, coil 76 may return to a starting position so as to allow lever arm 78 to catch a next tooth 82 of toothed wheel 72. Current in the first direction causes coil 76 to repeat the discrete movement, causing toothed wheel 72 to move through a next discrete rotational motion. As coil 76 moves back and forth, toothed wheel 72 is incrementally rotated in a plurality of discrete rotational motions, thereby rotating cam 70 in a respective plurality of discrete rotational motions so as to drive plunger 34 to deliver therapeutic substance 22 from pump chamber 28 to the subject in a plurality of discrete motions of plunger 34.

The accuracy of this system is defined by full discrete motions of coil 76 and not by analog continuous motions, as in many other drive systems. The discrete motions of coil 76, which drive toothed wheel 72 to rotate in discrete rotational motions, provide equal bolus steps making the flow of therapeutic substance uniform, i.e., accurate and continuous with little variation. The only control parameter that is used for different flow rates is the time per step, which can be controlled with software.

Opening and closing the inlet and outlet valves may similarly be controlled using a cam and moving-coil motor. For some applications, the same cam 70 and moving-coil motor 74 that are used to control plunger 34 are coupled to the valves and configured to open and close the respective valves in accordance with the various pumping phases as described hereinabove. Alternatively or additionally, some or all of the valves may be coupled to a dedicated valve cam and separate moving-coil motor for controlling the timing of the opening and closing of the respective valves.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method of delivering a therapeutic substance to a subject, the method comprising:
    using a plunger to draw the therapeutic substance from a therapeutic substance reservoir into a pump chamber of an electromechanical pumping assembly during a first pumping phase,
        the plunger being disposed such that therapeutic substance in the pump chamber is in direct contact with the plunger, and
        the pump chamber being in fluid communication with the reservoir and not in fluid communication with the subject during the first pumping phase; and
    subsequently, delivering the therapeutic substance from the pump chamber to the subject in a plurality of discrete dosages by delivering the therapeutic substance from the pump chamber in a plurality of discrete motions of the plunger during a second pumping phase, the pump chamber being in fluid communication with the subject and not in fluid communication with the reservoir during the second pumping phase, the method further comprising reducing an amplitude of negative pressure in the pump chamber during a negative-pressure reduction phase between the first pumping phase and the second pumping phase, by maintaining the pump chamber in fluid communication with the reservoir and not in fluid communication with the subject following the drawing of the therapeutic substance into the pump chamber, wherein maintaining the pump chamber in fluid communication with the reservoir and not in fluid communication with the subject comprises, following the drawing of the therapeutic substance into the pump chamber, using control circuitry to:
  (a) maintain open an inlet valve, the inlet valve disposed in a therapeutic substance inlet of the pump chamber through which the therapeutic substance is received from the reservoir into the pump chamber during the first pumping phase, and
  (b) maintain closed an outlet valve, the outlet valve disposed in a therapeutic substance outlet of the pump chamber through which the therapeutic substance is delivered from the pump chamber to the subject during the second pumping phase.

2. The method according to claim 1, wherein:
  (a) using the plunger to draw the therapeutic substance from the therapeutic substance reservoir into the pump chamber comprises (i) opening the inlet valve, and (ii) closing the outlet valve, and
  (b) delivering the therapeutic substance from the pump chamber to the subject comprises closing the inlet valve and opening the outlet valve.

3. The method according to claim 1, wherein using the plunger to draw the therapeutic substance from the therapeutic substance reservoir into the pump chamber comprises using the plunger to draw the therapeutic substance from the therapeutic substance reservoir into the pump chamber in a single motion of the plunger.

4. The method according to claim 1, wherein using the plunger to draw the therapeutic substance from the therapeutic substance reservoir into the pump chamber comprises using the plunger to draw the therapeutic substance from the therapeutic substance reservoir into the pump chamber in one or more discrete expansion motions of the plunger, wherein each expansion motion is longer in duration than any one of the plurality of discrete motions of the plunger during the second pumping phase.

\* \* \* \* \*